United States Patent [19]

Schanz et al.

[11] Patent Number: 4,539,195

[45] Date of Patent: Sep. 3, 1985

[54] BASIC MAGNESIUM ALUMINUM HYDROXYCARBONATE

[75] Inventors: Klaus Schanz, Dannstadt-Schauernheim; Albert Schwind, Bad Dürkheim; Hartmut Grund, Waldsee; Peter Klehr, Ludwigshafen am Rhein, all of Fed. Rep. of Germany

[73] Assignee: Giulini Chemie GmbH, Ludwigshafen am Rhein, Fed. Rep. of Germany

[21] Appl. No.: 582,773

[22] Filed: Feb. 23, 1984

[30] Foreign Application Priority Data

Feb. 26, 1983 [DE] Fed. Rep. of Germany ....... 3306822

[51] Int. Cl.³ ................. A01N 59/06; C01F 5/24; C01F 11/18; C01F 7/02
[52] U.S. Cl. ................. 423/419 P; 423/430; 423/431; 423/629; 424/156; 424/157
[58] Field of Search ........... 423/115, 129, 410 R, 423/419 P, 430, 431, 600, 631; 424/154, 156, 157

[56] References Cited

U.S. PATENT DOCUMENTS 2,797,978 7/1957 Beekman .................... 423/430
3,857,938 12/1974 Rouati et al. ................. 424/157
4,447,417 5/1984 Spickett et al. ............... 423/430

FOREIGN PATENT DOCUMENTS 1592126 6/1977 Fed. Rep. of Germany .
2905256 8/1979 Fed. Rep. of Germany .
1532167 7/1967 France ........................ 423/419 P
50-30039 9/1975 Japan ........................... 423/419 P
1086779 10/1967 United Kingdom .
1185920 3/1970 United Kingdom .
1598375 9/1981 United Kingdom .

Primary Examiner—Gary P. Straub
Attorney, Agent, or Firm—Spencer & Frank

[57] ABSTRACT

Crystalline, basic magnesium aluminum hydroxycarbonate of the formula

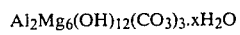

$$Al_2Mg_6(OH)_{12}(CO_3)_3 \cdot xH_2O$$

where x is at least 4. A process for producing it comprises the conversion of aluminum hydroxide with basic magnesium carbonate and at least one compound selected from magnesium hydroxide and magnesium oxide. Stoichiometric quantities are employed with reference to the aluminum and the magnesium. The conversion takes place at temperatures from 50° to 100° C., and the resulting product is subsequently spray dried.

7 Claims, No Drawings

BASIC MAGNESIUM ALUMINUM HYDROXYCARBONATE

BACKGROUND OF THE INVENTION

The present invention relates to crystalline magnesium aluminum hydroxycarbonate of the formula $$Al_2Mg_6(OH)_{12}(CO_3)_3 \cdot xH_2O \text{ or}$$
$$Al_2O_3 \cdot 6MgO \cdot 3CO_2 \cdot (x+6)H_2O,$$

respectively,
in which x is at least 4,
as well as to a process for manufacturing the product and antacids containing it.

Basic magnesium aluminum carbonates are known. For example, British Pat. No. 1,086,779 discloses carbonates of the formula $$Al_2O_3 \cdot xMgO \cdot yCO_2 \cdot zH_2O,$$

where x can be 0.15 to 1.5, y varies from 0.3 to 2.5 and z is no less than 2.5. These compounds are produced by conversion of magnesium carbonate, magnesium bicarbonate or a mixture of the two carbonates with an aqueous aluminum salt solution. British Pat. No. 1,086,779 states that it is of importance that the magnesium ions are present in quantities which are above the stoichiometrically required quantity in order to obtain products which contain magnesium. For 1 equivalent aluminum ions, 1.05 to 1.5 or more equivalents of magnesium ions are used. After precipitation, the basic carbonates are filtered out, washed and dried. They contain no more than 0.05 Mol % sodium and are suitable for use as antacid.

As a result of contacting the magnesium carbonate or bicarbonate with the aluminum salt, the magnesium aluminum hydroxy carbonates are obtained as a precipitate in the reaction mass. The mass may be filtered, washed, and dried in accordance with known techniques to obtain the final product, or it may be filtered, washed, and repulped to an aqueous slurry, or paste, to be incorporated in liquid antacids.

British Pat. No. 1,185,920 and corresponding DE-AS 1,592,126 disclose a process for preparing hydrotalcite which is known as a mineral having a chemical structure of the formula $$Mg_6Al_2(OH)_{16}CO_3 \cdot 4H_2O \text{ or}$$
$$Al_2O_3 \cdot 6MgO \cdot CO_2 \cdot 12H_2O.$$

The process comprises forming a mixture, of pH at least 8, of an aluminum component selected from aluminum hydroxide, basic aluminum carbonate aluminum hydroxide - alkalimetal carbonate complexes, aluminum amino acid salts, aluminum alcoholate, water-soluble aluminates, aluminum nitrate, and aluminum sulphate, with a magnesium component selected from magnesium oxide, magnesium hydroxide, neutral and basic magnesium carbonates and water-soluble magnesium salts, in an aqueous medium in the presence of carbonate ion in a ratio in terms of $Al_2O_3:MgO$ of substantially 1:6, and recovering the precipitated product.

British Pat. No. 1,598,375 and corresponding DE-OS 29 05 256 discloses a crystalline basic aluminum magnesium carbonate of the formula $Al_2Mg_6(OH)_{14}(CO_3)_2 \cdot 4H_2O$.

The compound is prepared by a process which comprises heating a mixture of aluminum hydroxide and magnesium hydroxide in the appropriate molecular proportions in the presence of carbon dioxide in an aqueous medium containing ammonia or a water-soluble organic nitrogen-containing base at a temperature between 70° and 100° C. at atmospheric pressure, and separating from the reaction mixture the aluminum magnesium carbonate. The amount of ammonia or water-soluble organic base used is critical and quantities greater than 6 moles per mole of $Al_2O_3$ present in the reaction mixture are necessary to ensure complete reaction. On completion of the reaction, the product is collected by filtration, washed with water and dried to give the product. British Pat. No. 1,598,375 and corresponding DE-OS 29 05 256 provide X-ray diffraction spectra of the compound produced according to these patents, and of hydrotalcite, both synthetic and natural.

SUMMARY OF THE INVENTION

It is an object of the present invention to provide a basic magnesium aluminum carbonate which has a better or at least the same antacid effect and duration of effect as the prior art basic carbonates and, in particular, is more economical to produce.

Another object of the present invention is to provide a process for producing such a basic magnesium aluminum carbonate.

Additional objects and advantages of the present invention will be set forth in part in the description which follows and in part will be obvious from the description or can be learned by practice of the invention. The objects and advantages are achieved by means of the processes, products, instrumentalities and combinations particularly pointed out in the appended claims.

To achieve the foregoing objects and in accordance with its purpose, the present invention provides a basic magnesium aluminum hydroxy carbonate of the formula $Al_2Mg_6(OH)_{12}(CO_3)_3 \cdot xH_2O$ where x is at least 4.

The present invention further provides a method for producing such a magnesium aluminum hydroxycarbonate by providing an aqueous suspension containing active aluminum hydroxide, basic magnesium carbonate, and at least one compound selected from magnesium hydroxide and active magnesium oxide, in stoichiometric quantities with respect to the aluminum and the magnesium, converting the aluminum hydroxide, basic magnesium carbonate and the at least one compound at temperatures from 50° to 100° C. under the influence of shearing forces, and recovering the resulting product from the suspension by spray drying.

The conversion temperature advantageously is between 70° and 85° C. At the increased temperature, the reaction begins very rapidly and with a slight increase in viscosity. Catalysts or accelerators are not required.

DETAILED DESCRIPTION OF THE INVENTION

The aluminum magnesium carbonate of the present invention has the formula $$Al_2Mg_6(OH)_{12}(CO_3)_3 \cdot xH_2O$$

where x is at least 4.

A comparison of the X-ray diffraction spectra shows that the aluminum magnesium carbonate of the present invention has a different structure than the prior art compounds. Significant (intensive) lines of the hydrotalcite and of the carbonate according to DE-OS 2,905,256 are not present in the compound of the present invention and intensive lines of the novel compound of the present invention do not appear in the prior art compounds. X-ray diffraction spectra of natural hydrotalcite, compound $Al_2O_3.6MgO.Co_2.12H_2O$ (DE-AS 1,592,126), compound $Al_2Mg_6(OH)_{14}(CO_3)_2.4H_2O$ (DE-OS 2,905,256) and $Al_2Mg_6(OH)_{12}(CO_3)_3.H_2O$ according to the present invention are set forth below:

| Hydrotalcite ASTM CARD | Compound according to DE-AS 1,592,126 | Compound according to DE-OS 2,905,256 | Compound according to Present Invention |
|---|---|---|---|
| — | 7.75 | — | — |
| 7.69 | — | — | — |
| — | — | 7.595 | — |
| — | — | — | 7.495 |
| — | — | 5,752 | 5.777 |
| 3.88 | 3.89 | — | — |
| — | — | 3.817 | — |
| — | — | — | 3.779 |
| — | — | 2.893 | 2.906 |
| 2.58 | 2.59 | 2.563 | 2.588 |
| — | — | — | 2.573 |
| — | — | — | 2.555 |
| — | — | — | 2.543 |
| 2.30 | 2.30 | 2.291 | 2.292 |
| 1.96 | 1.96 | 1.941 | 1.936 |
| 1.53 | 1.53 | 1.525 | 1.519 |
| 1.50 | 1.50 | 1.496 | 1.489 |

The basic magnesium aluminum hydroxycarbonate of the present invention can be used as the active ingredient of an antacid and mixed with a pharmaceutically acceptable carrier or diluent to form a pharmaceutical composition.

It must be considered surprising that a new basic aluminum hydroxycarbonate can be produced by way of conversion of aluminum hydroxide with magnesium hydroxide and/or magnesium oxide as well as basic magnesium carbonate in stoichiometric quantities with respect to the aluminum and the magnesium; this could not be deduced from the prior art. It was not predictable that the substances, suspended in water in stoichiometric quantities with respect to the aluminum and the magnesium would react with one another and produce a new substance which has a better or at least the same antacid effect and duration of effect as the prior art basic carbonates. Under the given conditions, conversion is 100 percent. A crystalline product is obtained which contains no impurities and which, compared with prior art antacids, e.g. aluminum hydroxide gel and basic magnesium aluminum carbonates according to British Pat. No. 1,086,779, produces an effect which is of satisfactory duration and, most significantly, can be produced more cost efficiently.

The advantages of the novel process of the present invention is that the suspensions obtained from the conversion can be subjected to spray drying immediately at the end of the reaction. Filtration and expensive washing processes are not required.

Spray drying may take place in a spray dryer at entrance temperatures of 275° to 310° C. and exit temperatures of 105° to 110° C. However, these temperature ranges may also be exceeded in both directions.

The aluminum hydroxide employed is preferably an active aluminum hydroxide, particularly a finely particulate, amorphous aluminum hydroxide gel which quickly dissolves in diluted acid. Such an aluminum hydroxide can be produced, for example, by precipitation from aluminum salt solutions by means of bases, particularly alkali carbonates. The magnesium compounds employed in the process of the present invention should likewise be present in their active form. Dead-burnt MgO, for example, is entirely unsuitable. The production of active magnesium oxides (hydratable) and basic magnesium carbonates is known. If aluminum hydroxide is converted in the present invention with a mixture of a basic magnesium carbonate and magnesium oxide, the magnesium oxide provided by the basic magnesium carbonate should be between 44 and 70 weight percent of the total magnesium oxide.

Of course, in the novel compound of the present invention, the crystal water may be removed completely or in part by thermal treatments.

The present invention will now be explained in even greater detail with the aid of the following examples.

The following examples are given by way of illustration to further explain the principles of the invention. These examples are merely illustrative and are not to be understood as limiting the scope and underlying principles of the invention in any way. All percentages referred to herein are by weight unless otherwise indicated.

EXAMPLE 1

0.578 kg of a magnesium hydroxide paste having an MgO content of 21.0 weight percent, 4 kg of an aluminum hydroxide gel paste having an $Al_2O_3$ content of 10.25 weight percent (3.8 weight percent $CO_2$) and 2.002 kg basic magnesium carbonate having an MgO content of 42.3 weight percent and a $CO_2$ content of 37.0 weight percent are suspended in 13 liters of water. The suspension is heated to 85° C. under stirring for six hours.

After six hours, the volume of the suspension was 19 liters and the solids content at 80° C. was 13.1 weight percent. The viscosity of the suspension, measured in a Brookfield RV, Spindle III, was at 10 revolutions = 1000 cp
20 revolutions = 575 cp
50 revolutions = 286 cp
100 revolutions = 170 cp.

After spray drying, 2.73 kg of the novel product were available, which corresponds to a yield of 100%.

| Analysis | in practice | in theory |
|---|---|---|
| $Al_2O_3$ | 15.1% | 15.54% |
| MgO | 35.9% | 36.87% |
| $CO_2$ | 19.9% | 20.12% |

In the examples below, magnesium oxide is used instead of $Mg(OH)_2$.

EXAMPLE 2

6.838 kg aluminum hydroxide gel paste and 1.534 kg basic magnesium carbonate are suspended in 20 liters of water. The $Al_2O_3$ content of the paste is 8.95 weight % and the $CO_2$ content is 3.3 weight %.

The basic magnesium carbonate contains 42 weight % MgO and 37.0 weight % $CO_2$. Then, 0.835 kg of a commercially available active magnesium oxide are introduced into the suspension so that the proportion of MgO as basic magnesium carbonate is at 44.4 weight %. After indirect heating with steam to 85° C. (1 hour), the conversion took place in one hour at 85° C. under intensive stirring. The final volume lies at 26 to 27 liters.

During spray drying of the suspension, the entrance temperature is 280° to 290° C. and the exit temperature is 105° to 107° C.

An analysis of the spray dried products evidences an $Al_2O_3$ content of 14.9 weight %, a magnesium oxide content of 35.6 weight % and a $CO_2$ content of 17.6 weight %.

EXAMPLE 3

As in Example 2, aluminum hydroxide gel paste (6.838 kg) and basic magnesium carbonate (2.140 kg) are suspended in 20 liters of water.

The added quantity of magnesium oxide is 0.571 kg, so that the MgO proportion as basic magnesium carbonate is 62 weight %.

As in Example 1, the temperature of the suspension is brought to 85° C. by means of steam jacket heating. After a reaction time of two hours at this temperature and spray drying of the reaction product as in Example 2, a product is available whose $Al_2O_3$ content is 14.8 weight %. Its MgO content is 35.6 weight % and its $CO_2$ content is 18.1 weight %.

EXAMPLE 4

The proportion of magnesium oxide in the form of basic magnesium carbonate was increased further, namely to 90 weight %.

The process was started with 18 liters of water into which were stirred 150 g MgO that had been hydrated for 12 hours by storage in 2 liters of water. Thereafter, 5.564 kg aluminum hydroxide gel paste having an $Al_2O_3$ content of 11% and a $CO_2$ content of 4.1%, as well as 3.110 kg basic magnesium carbonate, were stirred in. The magnesium oxide content, as in Examples 2 and 3, is 42 weight % and the $CO_2$ content is 37.0 weight % $CO_2$.

After heating the suspension to 85° C., the suspension is stirred at this temperature for an additional 12 hours. Contrary to Examples 2 and 3, the conversion takes place very slowly. It is assumed that under the given test conditions, aging caused the initial formation of insoluble but finely dispersed aluminum hydroxide gel, which was slowly converted to the acid soluble basic magnesium aluminum hydroxycarbonate while releasing excess carbonic acid. As in Examples 2 and 3, the suspension is spray dried. The $CO_2$ content of the sprayed product is 18.8 weight %.

The above results show that the conversion rate depends on the reaction capability of the components. The reaction rate can be influenced considerably, for example, by the type and quantity of the magnesium oxide and/or magnesium hydroxide that is added.

The acid binding capacity of the magnesium aluminum hydroxycarbonates produced in the Examples was determined according to the Sjoegren test where the acid binding capability is measured per g of suspended antacid in dependence on time while keeping a constant pH (pH=3) with 0.1 n HCl/g. The results of the acid binding capacity tests are set forth below:

EXAMPLES

| | Consumption of 0.1 n HCl (ml) | | |
|---|---|---|---|
| | after 5 min. | after 10 min. | after 30 min. |
| 1 | 115 | 137 | 187 |
| 2 | 128 | 150 | 202 |
| 3 | 128 | 150 | 198 |
| 4 | 105 | 110 | 136 |

The acid binding capacity of the individual magnesium aluminum hydroxycarbonates is as follows:

| Example | Acid Binding Capacity in ml 0.1 n HCl/g |
|---|---|
| 1 | 256 |
| 2 | 256 |
| 3 | 257 |
| 4 | 258 |

It will be understood that the above description of the present invention is susceptible to various modifications, changes and adaptations, and the same are intended to be comprehended within the meaning and range of equivalents of the appended claims.

What is claimed is:

1. Crystalline, basic aluminum magnesium carbonate of the formula $$Al_2Mg_6(OH)_{12}(CO_3)_3 \cdot xH_2O$$

where x is at least 4.

2. An antacid containing the crystalline, basic aluminum magnesium carbonate defined in claim 1.

3. Process for producing a basic aluminum magnesium carbonate of the formula $$Al_2Mg_6(OH)_{12}(CO_3)_3 \cdot xH_2O$$

where x is at least 4
comprising: mixing together in an aqueous suspension active aluminum hydroxide, basic magnesium carbonate and at least one compound selected from magnesium hydroxide and active magnesium oxide, in stoichiometric quantities with respect to the aluminum and the magnesium, wherein the magnesium oxide provided by the basic magnesium carbonate is between 44 and 70 weight percent of the total magnesium oxide, converting the active aluminum hydroxide, basic magnesium carbonate and the compound or compounds selected from magnesium hydroxide and active magnesium oxide to the basic aluminum magnesium carbonate at temperatures from 50° to 100° C. under the influence of shearing forces, and directly recovering the resulting product having the formula $Al_2Mg_6(OH)_{12}(CO_3)_3 \cdot xH_2O$ from the suspension by spray drying.

4. Process as defined in claim 3, wherein the aluminum hydroxide is converted with a mixture of a basic magnesium carbonate and magnesium oxide.

5. Process as defined in claim 3, wherein the aluminum hydroxide is converted with a mixture of basic magnesium carbonate and magnesium hydroxide.

6. Process as defined in claim 3, wherein the conversion is performed at a temperature from 70° to 85° C.

7. Process as defined in claim 3, wherein the aluminum hydroxide is in the form of amorphous aluminum hydroxide gel.

* * * * *